(12) United States Patent
Truckai et al.

(10) Patent No.: US 11,089,951 B2
(45) Date of Patent: Aug. 17, 2021

(54) ENDOSCOPIC IMAGING AND DISPLAY SYSTEM

(71) Applicant: Meditrina, Inc., Cupertino, CA (US)

(72) Inventors: Csaba Truckai, Saratoga, CA (US); John H. Shadduck, Menlo Park, CA (US)

(73) Assignee: Meditrina, Inc., San Jose, CA (US)

(*) Notice: Subject to any disclaimer, the term of this patent is extended or adjusted under 35 U.S.C. 154(b) by 28 days.

(21) Appl. No.: 15/443,402

(22) Filed: Feb. 27, 2017

(65) Prior Publication Data

US 2017/0245737 A1 Aug. 31, 2017

Related U.S. Application Data

(60) Provisional application No. 62/300,528, filed on Feb. 26, 2016, provisional application No. 62/340,981, filed on May 24, 2016.

(51) Int. Cl.
*A61B 1/05* (2006.01)
*A61B 1/00* (2006.01)
*G02B 23/24* (2006.01)
*H04N 5/232* (2006.01)
*A61B 1/04* (2006.01)
*H04N 5/225* (2006.01)

(52) U.S. Cl.
CPC ............ *A61B 1/05* (2013.01); *A61B 1/00016* (2013.01); *A61B 1/00018* (2013.01); *A61B 1/00052* (2013.01); *A61B 1/00103* (2013.01); *A61B 1/00108* (2013.01); *A61B 1/042* (2013.01); *G02B 23/2484* (2013.01); *H04N 5/23293* (2013.01); *H04N 2005/2255* (2013.01)

(58) Field of Classification Search
CPC ... A61B 1/00016; A61B 1/00018; A61B 1/05; A61B 1/00045; A61B 1/00052; A61B 1/00103; A61B 1/00108; A61B 1/00114; A61B 1/008; A61B 1/042; G02B 23/2484; G02B 23/2453; H04N 2005/2255; H04N 5/23293; H04N 5/2256
See application file for complete search history.

(56) References Cited

U.S. PATENT DOCUMENTS

| | | | |
|---|---|---|---|
| 2003/0076410 A1* | 4/2003 | Beutter | H04N 7/183 348/65 |
| 2008/0195128 A1* | 8/2008 | Orbay | A61B 1/00048 606/170 |
| 2010/0145146 A1* | 6/2010 | Melder | A61B 1/00052 600/112 |
| 2016/0066815 A1* | 3/2016 | Mei | B25J 9/1689 600/424 |
| 2017/0245737 A1* | 8/2017 | Truckai | A61B 1/00052 |

* cited by examiner

*Primary Examiner* — Farzana Hossain
(74) *Attorney, Agent, or Firm* — Levine Bagade Han LLP

(57) ABSTRACT

Medical endoscope imaging systems and methods of using the same are disclosed. The imaging systems can have an endoscope having an image sensor, a display housing having an image display, a communication link configured to couple the image sensor to the image display, and a camera housing having a camera-sensor. The display housing can be configured to be detachably coupled to the camera housing. The camera-sensor can be configured to receive signals from the image display.

27 Claims, 7 Drawing Sheets

ENDOSCOPIC IMAGING AND DISPLAY SYSTEM

CROSS-REFERENCE TO RELATED APPLICATIONS

This application claims the benefit of U.S. Provisional Application No. 62/300,528, filed Feb. 26, 2016, and U.S. Provisional Application No. 62/340,981, filed May 24, 2016, both of which are herein incorporated by reference in their entirety.

FIELD OF THE INVENTION

The present invention generally relates to endoscopic viewing systems for use in diagnostic and therapeutic medical procedures. More specifically, the invention relates to an imaging and display system and coupler that provides a universal image communication link to allow a disposable endoscope to be used with any legacy video endoscopy system.

BACKGROUND OF THE INVENTION

It is well known that there can be significant public health benefits from early diagnosis and treatment of disorders in sites in a patient's body that are accessible with an endoscope having a working channel. For example, endoscopes can be used to diagnose and treat diseases in the urethra, bladder, ureter, kidney, uterus, nasal passageways, sinuses, esophagus, stomach, colon, lungs, bronchi and other body passageways, cavities and spaces.

A typical endoscope comprises a flexible sleeve with a fiber optic light guide that guides light from an external light source to the endoscope tip to illuminate the working space in the patient's body. Such an endoscope can have an imaging sensor and optics at its distal tip to produce an image that is routed to a display, or the endoscope can have an objective lens and fiber optic light guide that communicates with a camera detachably coupled to an endoscope handle. A typical flexible endoscope has a distal articulating portion, with articulation forces created in the handle which are transmitted to the articulation portion by control cables (also referred to as pull-wires). The pull-wires allow the physician to steer the working end of the endoscope to direct and navigate the working end to visualize the targeted site. Endoscopes can further include working channels for introducing treatment tools into a working space.

In commercial re-useable endoscopes, there are a number of problems. Flexible endoscopes are expensive devices and a paramount problem is sterilization of the endoscope following a procedure (if reused). Such sterilization requires tedious cleaning of the working channel with a brush followed by steam sterilization or another form of sterilization. Further, re-usable endoscopes are fragile and frequently damaged during use and particularly during the sterilization process.

Disposable endoscopes have been developed, and are often called a "chip on a stick" with an imaging sensor carried at the distal end of the endoscope. While disposable endoscopes can be economical and advantageous over the reusable endoscopes, one problem disposable endoscopes have is that they are not adaptable for use with the legacy video endoscopic systems that are in use in hospital operating rooms and surgery centers. What is needed is a disposable endoscope and imaging system that allows for coupling to multiple different legacy video endoscopic systems found in hospital operating rooms.

BRIEF SUMMARY OF THE INVENTION

Medical endoscope imaging systems and methods of using the same are disclosed.

The imaging systems can have an endoscope having an image sensor, a display housing having an image display, a communication link configured to couple the image sensor to the image display, and a camera housing having a camera-sensor. The display housing can be configured to be detachably coupled to the camera housing. The camera-sensor can be configured to receive signals from the image display.

The methods can include transmitting signals from a first sensor to a first display, transmitting signals from the first display to a second sensor, and transmitting the signals received by the second sensor from the first display to a second display for observation. The second sensor can be detachably coupled to the first display.

The endoscope can have an elongated member having a proximal housing and a distal end, an image sensor disposed in the distal end, and an image display disposed in a proximal-facing recess of the proximal housing.

The endoscope imaging system can have an endoscope comprising an elongated member having a proximal housing and a distal end, an image sensor disposed in the distal end, and a video endoscopy camera-sensor body configured to be mated to the proximal housing. The mated proximal housing and video endoscopy camera-sensor body can be configured to provide a light-tight chamber between the image sensor and a camera-sensor.

DETAILED DESCRIPTION

Medical endoscope systems are disclosed. The medical endoscope systems can have a digital display component and coupler that provide for a universal image communication link to video endoscopy systems found in hospital operating rooms, ambulatory surgery centers and the like. For example, the medical endoscope systems can have a digital display component and coupler that provide for a universal image communication link to legacy and/or existing video endoscopy systems.

Figure 1:
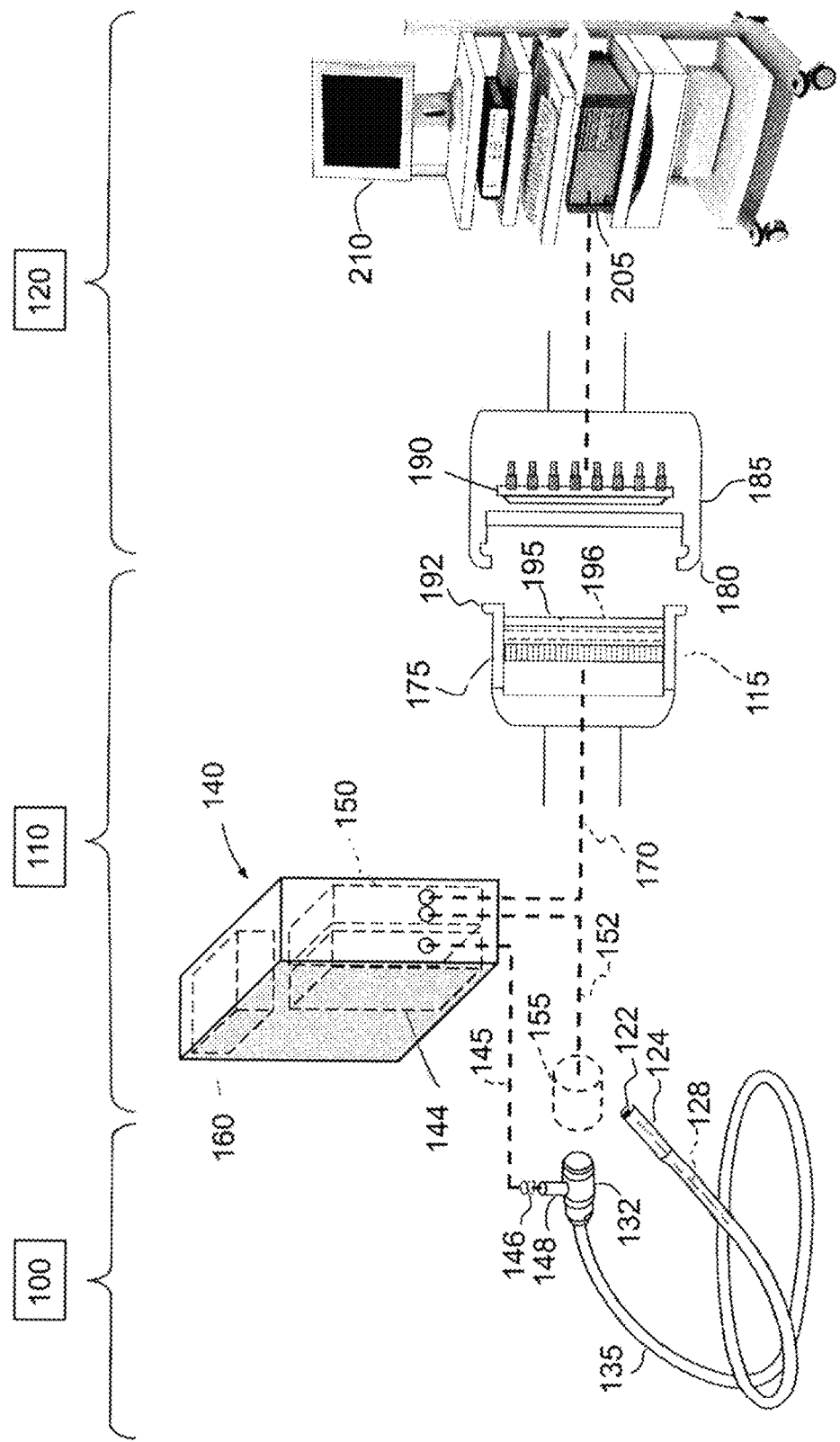
FIG. 1 illustrates a variation of an endoscopic imaging system having a disposable endoscope, an image receiving component and an image display component that can be detachably coupled with a C-mount or similar coupler to an imager of a commercially available video endoscopy system.

FIG. 1 is a schematic diagram of a variation of a medical endoscope system having various components. FIG. 1 shows that the system can comprise a disposable endoscope 100 and an image display system 110. The display system 110 can include a display housing 115 that is configured for detachable coupling to an existing or legacy endoscopic video system 120 (i.e., the display housing 115 can be detachably coupled to an existing or legacy endoscopic video system 120).

In FIG. 1, the endoscope 100 can be a rigid endoscope, a flexible endoscope or an articulating endoscope, although any type of endoscope is appreciated. The endoscope 100 can be a disposable endoscope or a re-useable endoscope. For example, the endoscope 100 can be sterilizable and thus re-usable for a number of uses. The endoscope 100 can have a digital image sensor 122, such as a complementary metal-oxide semi-conductor sensor (CMOS chip) at a distal end 124 of the endoscope 100. Electrical cables 128 can extend from the sensor 122 to/through the endoscope 100 to a proximal handle portion 132. FIG. 1 illustrates that the endoscope 100 can comprise a disposable flexible body 135. The endoscope body 135 can have a diameter from about 1 mm to about 4 mm. Other diameters, more or less, as well as other ranges, narrower or wider, are also appreciated. For example, in a variation useful for urology (among other applications), the endoscope 100 can have a diameter of about 2.0 mm with a 1.0 mm working channel, a fluid inflow channel and a pressure sensing channel. The endoscope body 135 can carry, enclose, or otherwise house light fibers for illuminating a working space.

Referring again to FIG. 1, the digital display system 110 can include a control unit or base unit 140 that carries/houses subsystems that enable use of the endoscope 100. For example, the base unit 140 can house a light source 144 that carries light through a light cable 145 to a connector 146 that detachably couples to the light fitting 148 on the handle portion 132 of the endoscope 100. The light source 144 can comprise one or more LEDs that are coupled to light fibers in the light cable 145. In a variation, the light source 144 can provide a maximum illumination of 2×150 lumens in two 0.5 mm diameter circular emitters. A fiber optic light collimator can be used to reduce the LED emitter surfaces to a 0.5 mm spot.

The base unit 140 can have a video microprocessor 150 for processing the image data stream from the image sensor 122 of the endoscope 100. For example, the base unit 140 can carry, enclose, or otherwise house the microprocessor 150. Similarly, the endoscope 100 can carry, enclose, or otherwise house the image sensor 122 (e.g., as shown in FIG. 1, the sensor 122 can be permanently or detachably coupled to the distal end 124 of the endoscope 100). A data transmission cable 152 can extend from the base unit 140 to a connector 155 that connects to the handle portion 132 of the endoscope 100.

Still referring to FIG. 1, the base unit 140 can have a battery module 160 for powering the light source 144, the video microprocessor 150, and the systems communication link and the display as will be described below. For example, the base unit 140 can carry or house the battery module 160. The battery unit 160 can be re-charged as is known in the art, for example, by inductive coupling or by a cable to an electrical source. The battery module 160 can provide for an operating time of 2 hours or more with normal usage (e.g., 2 hours, 2.5 hours, 3.0 hours, among others). Other times for any type of usage, more or less, are also appreciated (e.g., 2 hours or more, 2 hours or less, 3 hours or less, 4 hours or less, among others). Power usage can be optimized, for example, through software-controlled standby modes, display dimming and LED dimming.

FIG. 1 shows that a digital transmission cable 170 can extend to a display 175 within a display housing 115. For example, the cable 170 can extend from the base unit 140 to the display 175. As can be seen in FIG. 1, the display housing 115 can be shaped and configured to be detachably coupled to a C-mount or other similar coupler portion 180 of a camera housing 185 that houses the camera-sensor 190, which is a standard component of a commercially available or legacy endoscopic video system 120.

FIG. 1 illustrates that the display housing 115 can have one or more flanges 192 that cooperate with one or more receiving features of the coupler portion 180 of the camera housing 185 of the endoscopic video system 120. The display housing 115 can carry or house the digital display 175. The digital display 175 can be a liquid crystal display (LCD), a liquid crystal on silicon display (LCOS) or an organic light-emitting diode display (OLED). In a variation, the display 175 can have a diagonal dimension of less than 2 inches, less than 1.5 inches or less than 1 inch. Such a display 175 can have at least 800×600 pixels. Other diagonal dimensions and pixel resolutions, more or less, as well as other ranges, larger or smaller, are also appreciated. For example, in a variation, the display 175 can have at least twice as many pixels as the camera-sensor 190 of the cooperating video endoscopy system 120 to minimize the Moire effect and to thus not limit resolution on the optical output side. The video processor 150 can be configured to process the sensor input image data and display it on a display (e.g., display 175) at at least a 30 fps (frames per second) rate.

The display 175 can be carried or housed in the display housing 115 in a configuration that provides complementary alignment with the camera-sensor 190 of the endoscopic video system 120. By the term alignment, it is meant that a centerline of the display 175 can be aligned with a centerline of the camera-sensor 190, and that a surface of display 175 can be parallel with a surface of the camera-sensor 190. Other alignments are also appreciated.

In a variation, the display housing 115 can carry or house the display 175 in a manually rotatable collar that can be manually rotated to angularly align the display 175 with the camera-sensor 190.

Figure 2:
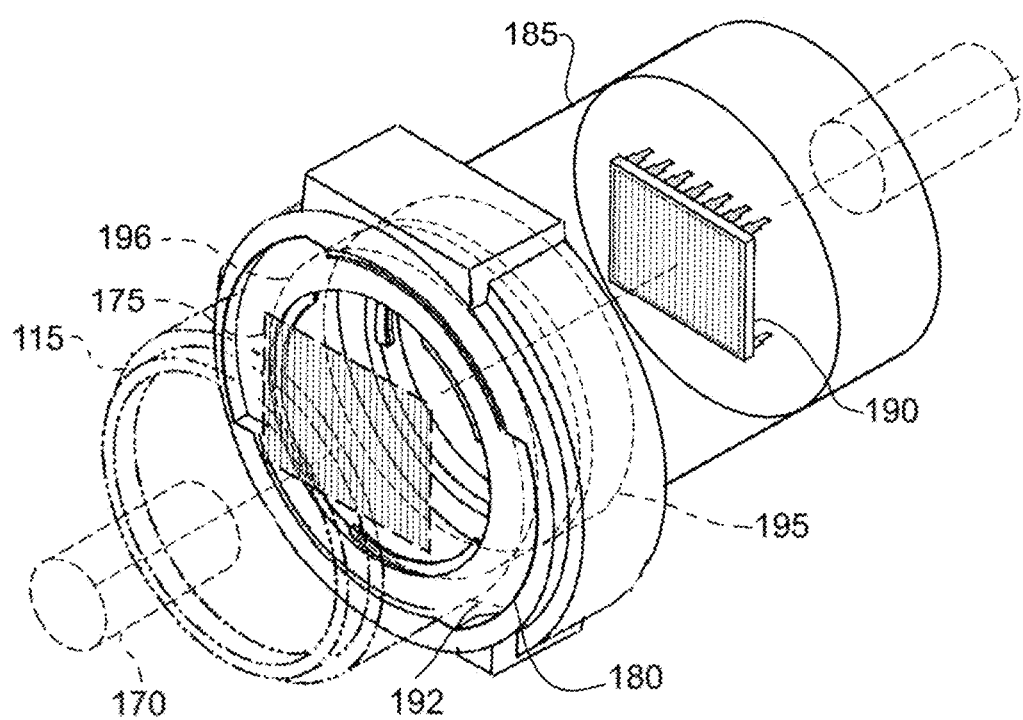
FIG. 2 illustrates an enlarged view of a variation of an image display component that can be detachably coupled with a C-mount or similar coupler to a camera-sensor camera of a video endoscopy system.

FIG. 2 shows an enlarged schematic view of a variation of the display housing 115 that can be coupled to a C-mount or coupler portion 180 of camera housing 185. It can be seen that the display 175 is positionable in alignment with the camera-sensor 190 when the two housings 115 and 185 are coupled together. Optical lenses 195 can be integrated into the display housing 115. In a variation, a moire fringe erasing filter 196 can be carried/housed in the display housing 115, as is known in the art.

It can be understood from FIGS. 1 and 2 that during use of the endoscope 100, digital imaging data is transmitted from the endoscope sensor 122 to the video processor 150 in the base unit 140, which in turn processes and transmits the data to provide a video image on the display 175. Concurrently, the camera-sensor 190 of the legacy video endoscopy system 120 images the display 175 and transmits its image data to a video processor 205 of the video endoscopy system 120 and then displays the images on a video display 210 (see, e.g., FIGS. 1 and 4). By this means, the use of the disposable endoscope 100 can be integrated into the existing video endoscopy system 120 which then allows the legacy system 120 to be used to display, record, and process the patient and procedure information as/as is needed for hospital record-keeping.

A sterile cover can be provided to cover the cables 145, 152, 170. The sterile cover can be disposable. For example, a disposable sterile cover can be provided to cover the cable 145 that extends from the base unit 140 to the endoscope 100, to cover the cable 152 that extends from the base 140 to the connector 155, and/or to cover the cable 170 that extends from the base unit 140 to the video endoscopy system 120.

Figure 3:
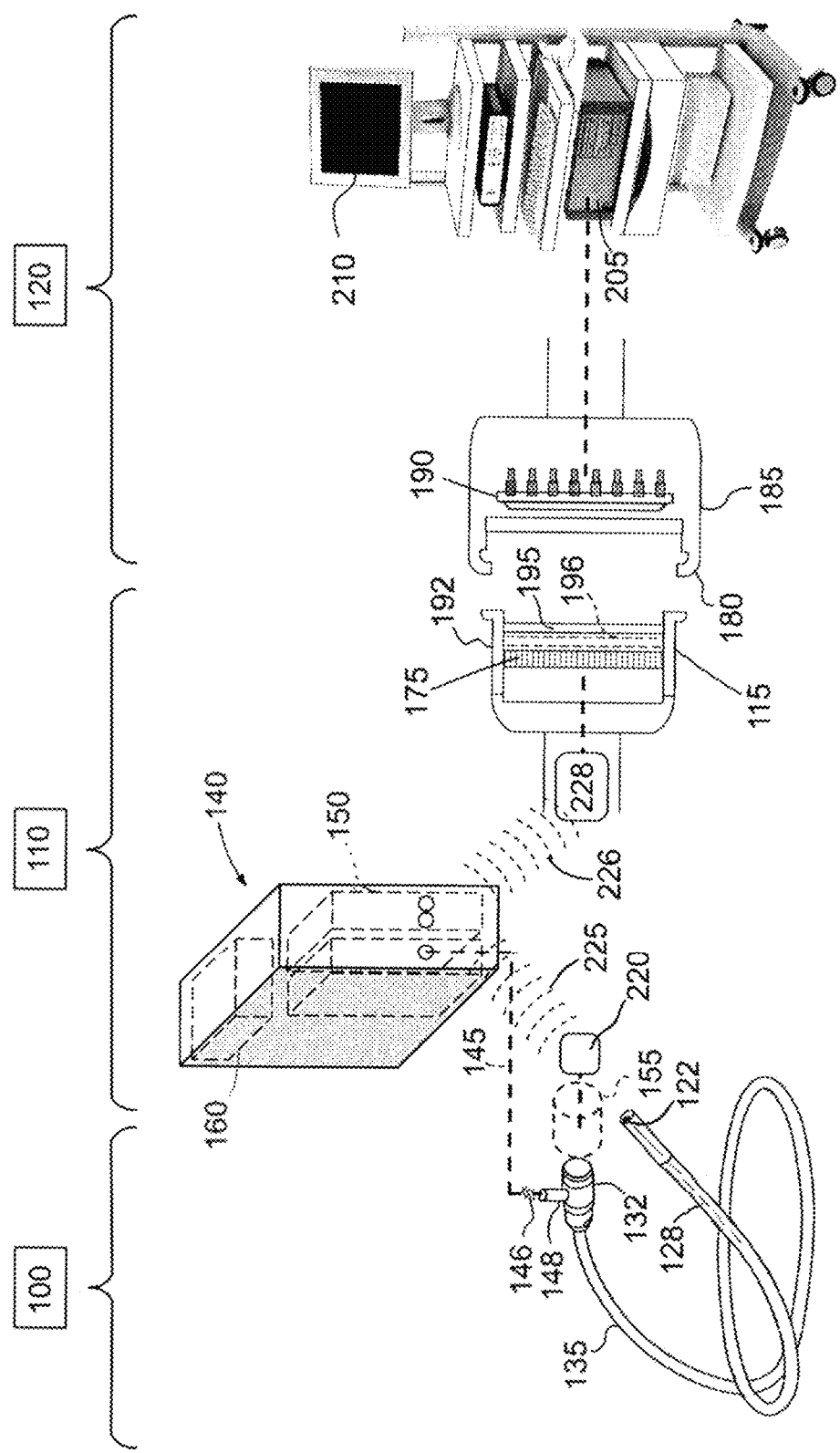
FIG. 3 illustrates a variation of the system of FIG. 1 having wireless communication links between various system components.

FIG. 3 shows a variation of the display system 110 which uses wireless data transmission between the system components rather than cables 152 and 170 shown in the system of FIG. 1. As shown in FIG. 3, the endoscope coupler 155 can include a wireless transmitter 220, such as Bluetooth or Wi-Fi, that can transmit image data signals 225 to the video processor 150. Similarly, the video processor 150 can include a transmitter for sending Bluetooth or Wi-Fi data signals 226 to a receiver 228 carried or housed by the display housing 115.

Figure 4:
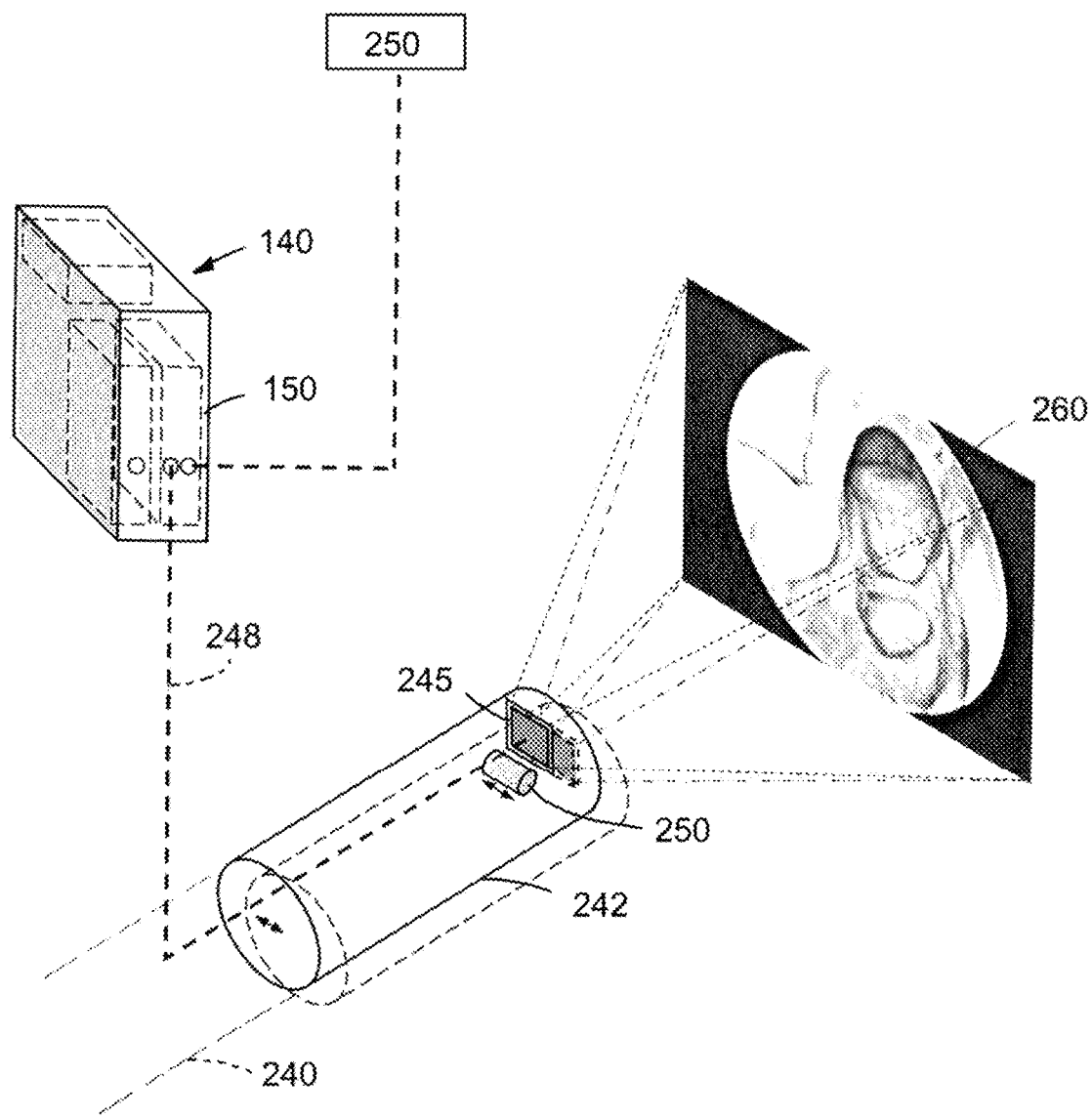
FIG. 4 illustrates a variation of the system in which a form of stereoscopic viewing is provided.

FIG. 4 illustrates a variation of an endoscope 240. The endoscope 240 can be functionally similar or identical to endoscope 100 and can have any of the features described above. For example, the endoscope 240 can be a rigid, flexible, articulating, disposable, re-useable, or a combination thereof. As shown in FIG. 4, the endoscope 240 can have a working end 242 that has an imaging sensor 245 as described above (e.g., with reference to imaging sensor 122). The sensor 245 can be connected by a cable 248 to a video processor 150 as described above. FIG. 4 illustrates that the endoscope working end 242 can have a piezoelectric element 250. The piezoelectric element 250 can be adapted to move the sensor 245 laterally and/or angularly. For example, the piezoelectric element 250 can be adapted to move the sensor 245 laterally and/or angularly at a high repetition rate. The sensor 245 can move a selected dimension or degree to provide at least a 5° change in viewing angle relative to a targeted site indicated by image 260. Other degree changes, more or less, as well as other ranges, narrower or wider, are also appreciated (e.g., at least a 7° change, at least a 10° change, among others).

As can be understood from FIG. 4, the image data transmitted to the video processor 150 from sensor 245 will/can be from different angles relative to the target site. The video processor 150 can include one or more algorithms to select image data from the sensor 245 in first and second positions in which the sensor 245 is furthest laterally or angularly spaced apart. The video processor 150 can display the selected data as two video images in a stereoscopic manner in two displays, or a single display 260, to provide the viewer with a 3D or stereoscopic view of the target site It should be appreciated that the endoscope 100 and imaging display system 110 can be used together with an electrosurgical probe introduced through the working channel of the endoscope 100. When such electrosurgical devices are used in close proximity to an imaging sensor 122 as described above, there is a potential for electrical interference with the imaging chip. For that reason, the endoscope 100 and/or components of the imaging display system 110 can be provided with electromagnetic interference shielding (e.g., EMI shielding) that can cover and surround the various system components. Electronic shielding is known in the art and can be a thin polymer layer layers containing conductive metallic powders, wire mesh components or the like. Such shielding systems can be designed or provided by one of the following companies: Holland Shielding Systems BV, Jacobus Lipsweg 124, 3316BP Dordrecht, Netherlands; Optical Filters USA, 13447 South Mosiertown Road, Meadville Pa. 16335; or Parker Chomerics, 6 Flagstone Dr, Hudson, N.H. 03051, among others.

Figure 5:
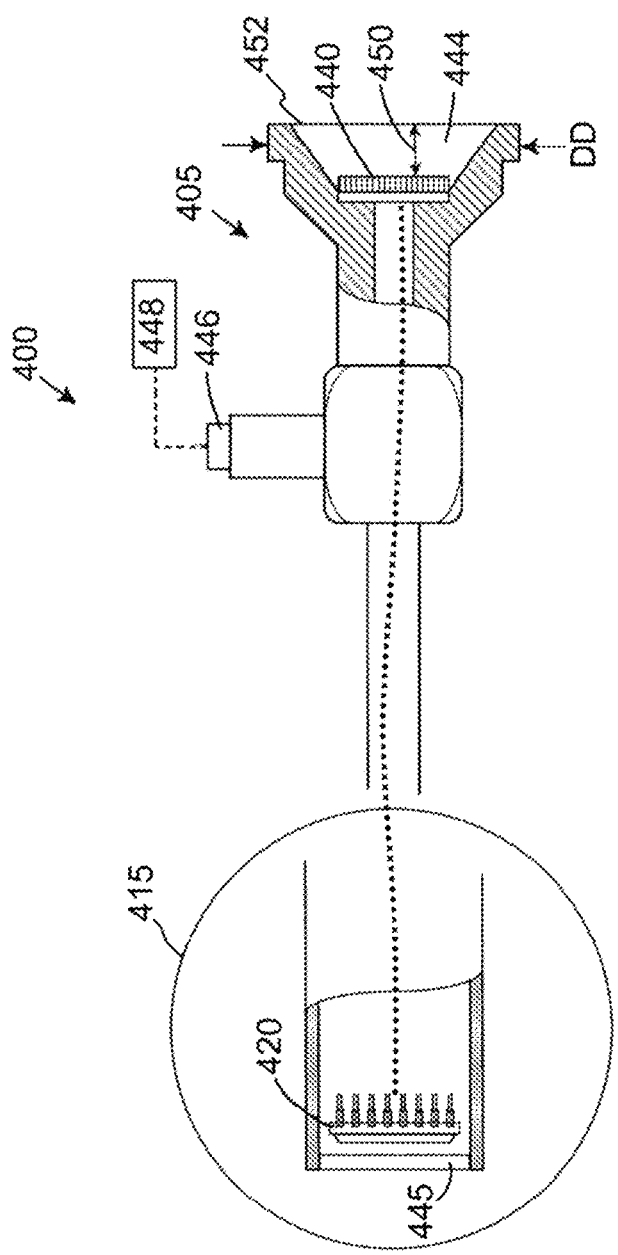
FIG. 5 illustrates a variation of an endoscope having a display and an eyepiece.
Figure 6:
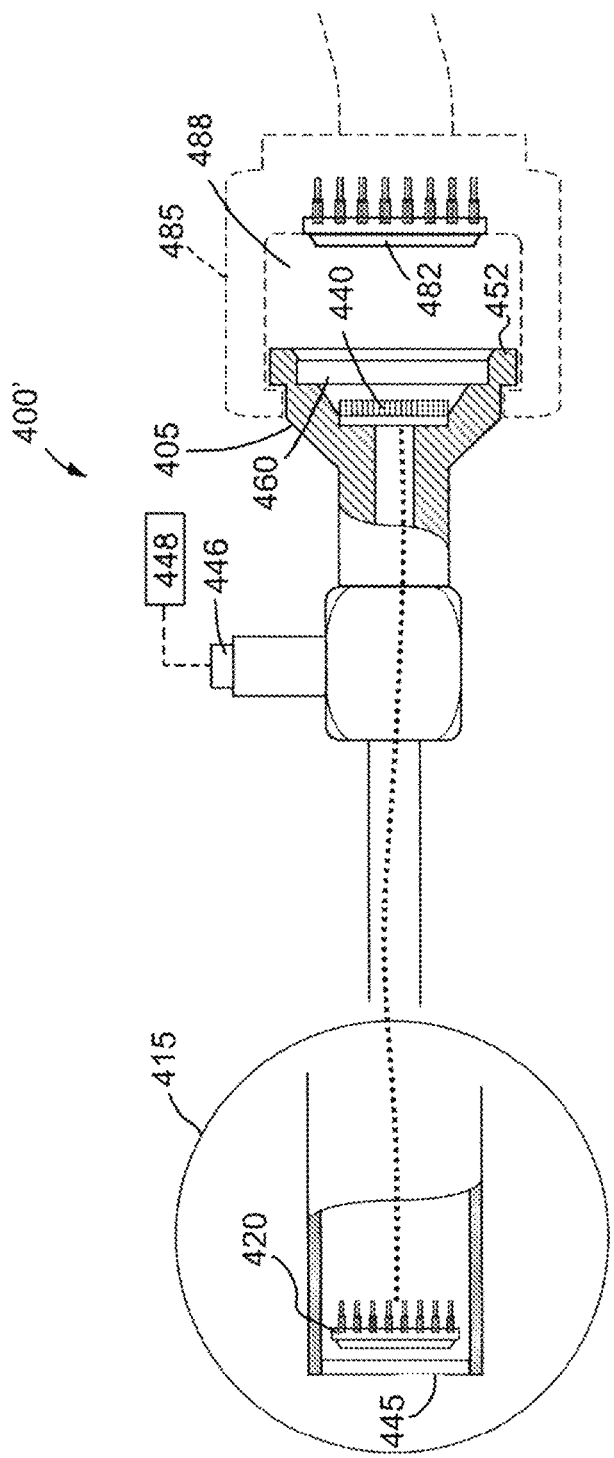
FIG. 6 illustrates a variation of an endoscope having a de-focusing lens.
Figure 7:
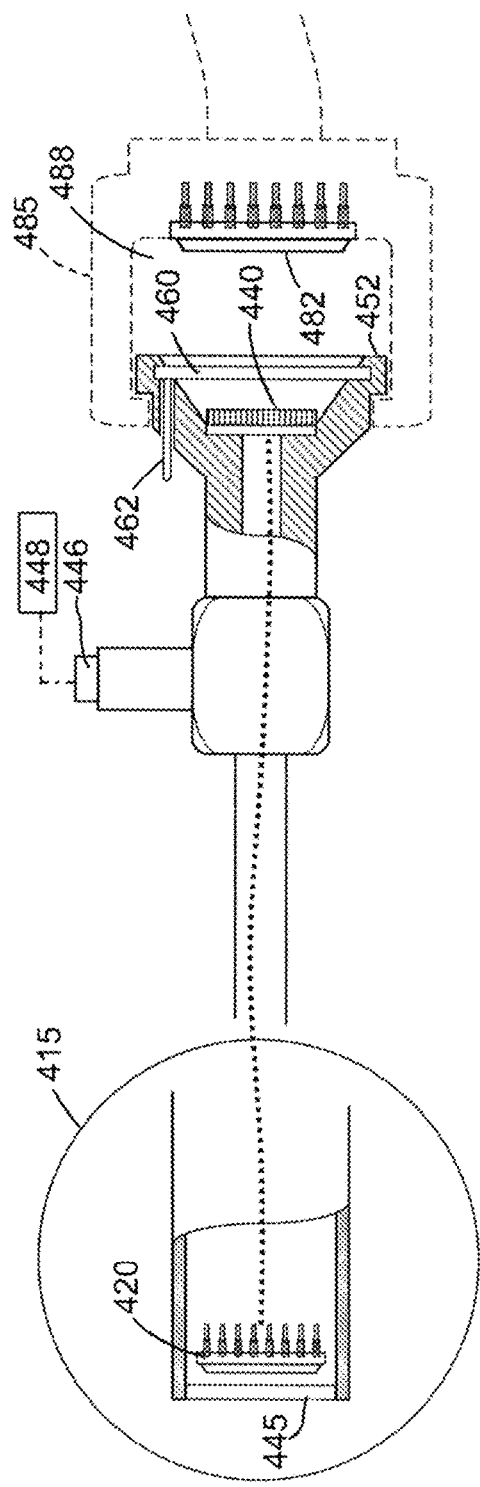
FIG. 7 illustrates a variation of an endoscope having a light-tight assembly.

Now turning to FIGS. 5-7, another aspect of the medical endoscope systems disclosed herein relates to the physical dimensions and characteristics of an endoscope 400 and particularly the proximal housing 405 or handle of the endoscope. As shown, the endoscope 400 can comprise an elongated member 410 with a proximal housing 405 and a distal end 415, an image sensor 420 carried or housed in the distal end 415 and an image display 440 carried or housed in a proximal-facing recess 444 in/of the housing 405. The image sensor 420 can be carried or disposed inward (e.g., toward the proximal housing) of a lens assembly 445 (not to scale) in the endoscope shaft. A light connection 446 can be provided as is known in the art to carry light from a source 448 to optic fibers in the endoscope. In a variation, the image display 440 can have a diagonal dimension of less than 1.0 inch, less than 0.9 inches or less than 0.8 inches. The image display 440 can have at least 800×600 pixels. Other diagonal dimensions and pixel resolutions, more or less, as well as other ranges, larger or smaller, are also appreciated. The endoscope housing 405 can have an exterior diagonal dimension (DD) of less than 2.5 inches, less than 2.0 inches or less than 1.5 inches. Other diagonal dimensions, more or less, as well as other ranges, narrower or wider, are also appreciated.

Still referring to FIG. 5, the proximal-facing recess 444 can be configured such that the spacing 450 from a proximal surface of the image display 440 to a proximal face of the housing 452 is at least 0.2 inches. Other dimensions for spacing 450, more or less, as well as other ranges, narrower or wider, are also appreciated. For example, the spacing 450 can be at least 0.4 inches or at least 0.6 inches, among other values and ranges.

FIG. 6 illustrates a variation of an endoscope 400' having a de-focusing lens 460 proximate the image display 440. Such a de-focusing lens 460 can be carried by or housed in the housing proximal to the image display. FIG. 7 shows that the de-focusing lens 460 can comprise an assembly of lens that allows for adjustment of the defocus level by an actuator mechanism 462 shown in carried by the housing proximal to the image display.

The endoscope (e.g., endoscope 100, 240, 400, 400') can have an elongated member that comprises a rigid assembly. The elongated member can comprise a flexible assembly that can and be articulated by an actuation mechanism in the handle as is known in the art.

Referring to FIG. 7, the endoscope 400' can be configured to be mated to a video endoscopy camera-sensor 482 in body 485. The body 485 can be configured to be mated to the housing (e.g., housing 405), and when the endoscope housing 405 and the camera-sensor body 485 are mated, the coupling can provide a light-tight chamber 488 between the image display 440 and the camera-sensor 482. A number of embodiments of the invention have been described. Nevertheless, it will be understood that various modifications may be made without departing from the spirit and scope of the invention.

Like reference numerals in the drawings indicate identical or functionally similar features/elements.

All dimensions disclosed herein are exemplary. The dimensions disclosed herein can at least be expanded to ranges from about 50% to about 150% of the exemplary dimension shown herein, more narrowly from about 75% to about 125% of the exemplary dimension shown herein.

Language such as "at least," "greater than," "less than," "between," and the like includes the number recited.

The words "may" and "can" are interchangeable (e.g., "may" can be replaced with "can" and "can" can be replaced with "may"). Any elements described herein as singular can be pluralized (e.g., anything described as "one" can be more than one, anything referred to with an indefinite article, e.g., "a" or "an," can be more than one, anything referred to with the definite article "the" can be more than one, etc.). Any species element of a genus element can have the characteristics or elements of any other species element of that genus.

The above-described and illustrated features, elements, configurations, assemblies, sub-assemblies, complete assemblies, and/or methods and their elements for carrying out the invention can be combined and/or modified with each other in any combination. Any of the below claims can be combined and/or modified with each other in any combination, as well as combined and/or modified with any other portion of the disclosure in any combination. The below claims are exemplary and not limiting.

What is claimed is:

1. An endoscopic imaging system comprising:
   an endoscope having an image sensor;
   a display housing having an image display configured to display an image from the image sensor;
   a communication link configured to couple the image sensor to the image display; and
   a camera housing having a camera-sensor, wherein the display housing is configured to be detachably coupled to the camera housing, such that when coupled, the camera-sensor is aligned with the image display to permit the camera-sensor to transmit image data of the image and the image display is confined completely within the camera housing and the display housing.

2. The endoscopic imaging system of claim 1, wherein the image display is a liquid crystal display (LCD), a liquid crystal on silicon display (LCOS), or an organic light-emitting diode display (OLED).

3. The endoscopic imaging system of claim 1, wherein the image sensor is a complementary metal-oxide semi-conductor sensor.

4. The endoscopic imaging system of claim 1, wherein the communication link is an electrical cable.

5. The endoscopic imaging system of claim 1, wherein the communication link is a wireless link.

6. The endoscopic imaging system of claim 1, wherein the image display has a diagonal dimension of less than 2.0 inches, less than 1.5 inches, less than 1.0 inch, less than 0.9 inches, or less than 0.8 inches.

7. The endoscopic imaging system of claim 1, wherein the image display has at least 800×600 pixels.

8. The endoscopic imaging system of claim 1, further comprising a moire fringe erasing filter coupled to the display housing.

9. The endoscopic imaging system of claim 1, wherein the endoscope comprises a rigid endoscope, a flexible endoscope, or an articulating endoscope, and wherein the image sensor is housed in, coupled to, or carried in the endoscope.

10. The endoscopic imaging system of claim 1, wherein a surface of the image display is in complementary alignment with a surface of the camera-sensor.

11. The endoscopic imaging system of claim 10, wherein the image display is rotatable within the display housing such that the image display is rotatable relative to the camera-sensor.

12. The endoscopic imaging system of claim 10, wherein the display housing comprises a wireless component for receiving signals from a transmitting component coupled to the image sensor.

13. The endoscopic imaging system of claim 10, wherein the display housing is detachably coupled to the camera housing with a C-mount.

14. An endoscopic imaging method comprising:
   transmitting signals from an image sensor to a display housing having an image display that produces a first image;
   detachably coupling a camera housing having a camera sensor to the image display such that the camera sensor can generate a signal of the first image, when the image display is coupled to the camera sensor; and
   wherein when coupled, the camera-sensor is aligned with the image display to permit to the camera sensor to transmit the signal of the first image and the image display is confined completely within the camera housing and the display housing.

15. An endoscope comprising:
   an elongated member having a proximal housing and a distal end;
   an image sensor disposed in the distal end;
   an image display disposed in a proximal-facing recess of the proximal housing where the image display generates an image from the image sensor; and
   wherein the proximal housing is detachably coupled to a camera housing such that when coupled, the camera-sensor is aligned with the image display to permit the camera sensor to transmit image data of the image and the image display is confined within the camera housing and the display housing.

16. The endoscope of claim 15, wherein the image display has a diagonal dimension of less than 1.0 inch, less than 0.9 inches, or less than 0.8 inches.

17. The endoscope of claim 15, wherein the image display has at least 800×600 pixels.

18. The endoscope of claim 15, wherein the proximal-facing recess is configured such that a spacing from a proximal surface of the image display to a proximal face of the proximal housing is at least 0.2 inches.

19. The endoscope of claim 18, wherein the spacing is at least 0.4 inches.

20. The endoscope of claim 18, wherein the spacing is at least 0.6 inches.

21. The endoscope of claim 15, further comprising a de-focusing lens proximate the image display.

22. The endoscope of claim 15, further comprising a de-focusing lens disposed in the proximal housing proximal to the image display.

23. The endoscope of claim 15, further comprising an adjustable de-focusing lens assembly disposed in the proximal housing proximal to the image display.

24. The endoscope of claim 15, wherein the elongated member comprises a rigid assembly.

25. The endoscope of claim 15, wherein the elongated member comprises a flexible assembly.

26. The endoscope of claim 15, wherein the elongated member comprises an assembly that can be articulated by an actuation mechanism.

27. The endoscope of claim 15, wherein the housing has a diagonal dimension of less than 2.5 inches, less than 2.0 inches, or less than 1.5 inches.

* * * * *